United States Patent [19]

Ramstack

[11] Patent Number: 4,753,733
[45] Date of Patent: Jun. 28, 1988

[54] PLASMAPHERESIS METHOD AND APPARATUS FOR OVERCOMING MEMBRANE FOULING

[75] Inventor: Joseph M. Ramstack, West Chester, Pa.

[73] Assignee: E. I. Du Pont de Nemours and Company, Wilmington, Del.

[21] Appl. No.: 885,396

[22] Filed: Jul. 18, 1986

Related U.S. Application Data

[63] Continuation of Ser. No. 308,055, Oct. 2, 1981, abandoned.

[51] Int. Cl.[4] ............................................. B01D 13/00
[52] U.S. Cl. ...................................... 210/636; 210/637; 210/651; 210/321.69
[58] Field of Search ................ 210/636, 637, 649–655, 210/321, 416, 433, 321.69

[56] References Cited

U.S. PATENT DOCUMENTS

| | | | |
|---|---|---|---|
| 3,853,756 | 12/1974 | Stana | 210/433 X |
| 4,001,117 | 1/1977 | Trechsel | 210/180 |
| 4,075,091 | 2/1978 | Bellhouse | |
| 4,191,182 | 3/1980 | Popovich et al. | |
| 4,212,743 | 7/1980 | Van Meter et al. | 210/288 X |

FOREIGN PATENT DOCUMENTS 1381410  1/1975  United Kingdom ............... 210/636

OTHER PUBLICATIONS

Castino, F. et al., "The Filtration . . . ", in Art. Kid., Art. Liver and Art. Cells, edit. by T. M. S. Chang, Plenum Press, N.Y. (1978).
Asanuma, Y. et al, "Membrane Plasmapheresis . . . ", Proc. Eur. Soc. Artif. Intern. Organs, 6, 308–312, 1979.
Werynski, A. et al, "Membrane Plasma Separation . . . ", T.A.S.A. Intern. Organs, vol. 27, pp. 539–543, May 6–8, 1981.

*Primary Examiner*—Frank Spear

[57] ABSTRACT

Plasmapheresis by filtration can be carried out with high efficiency for long periods by conducting blood over a surface of a membrane and passing plasma at an accelerating rate until the threshold level is attained, maintaining the rate of passing plasma until the ceiling system transmembrane pressure difference is attained and then reducing the passing of plasma and the system transmembrane pressure difference and allowing the membrane to clear before repeating the cycle.

8 Claims, 2 Drawing Sheets

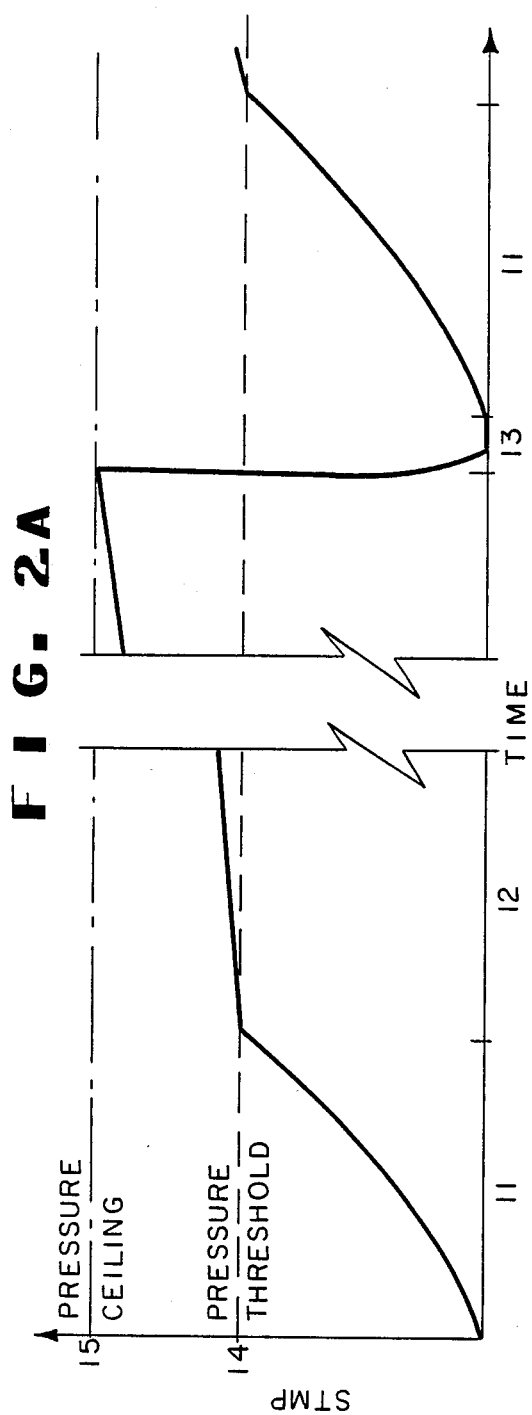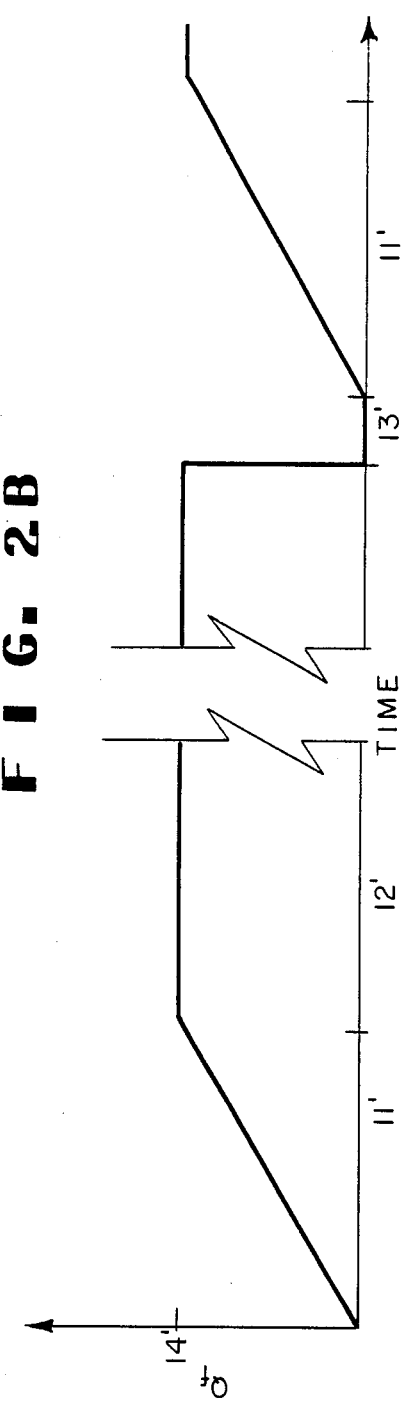

PLASMAPHERESIS METHOD AND APPARATUS FOR OVERCOMING MEMBRANE FOULING

This is a continuation of application Ser. No. 308,055 filed Oct. 2, 1981 and now expressly abandoned.

FIELD OF THE INVENTION

This invention relates to plasmapheresis by filtration.

BACKGROUND INFORMATION

Plasmapheresis is a process of separatihg plasma from whole blood. The plasma-depleted blood is comprised principally of cellular components, i.e., red blood cells, white blood cells and platelets. Plasma is comprised largely of water, but also contains proteins and various other noncellular compounds, both organic and inorganic.

Continuous plasmapheresis is a process of continuously removing whole blood from a subject, separating plasma from the blood and returning the plasma-depleted blood to the subject in a continuous extracorporeal circuit.

Plasmapheresis is currently used to obtain plasma for various transfusion needs, for preparation of fresh-frozen plasma, for subsequent fractionation to obtain specific proteins such as serum albumin, to produce cell culture media, and for disease therapies involving either the replacement of plasma or removal of specific disease-contributing factors from the plasma.

Plasmapheresis can be carried out by centrifugation or by filtration. Generally, in known filtration apparatus, whole blood is conducted in a laminar flow path across one surface, i.e., the blood side surface, of a micro-porous membrane filter. Useful micro-porous membrane filters have pores which substantially retain the cellular components of blood but allow plasma to pass through. Such pores are referred to herein as cell-retaining pores. Typically, cell-retaining pore diameters are 0.1 $\mu$m to 1.0 $\mu$m.

Various filtration devices for plasmapheresis are disclosed in the literature. U.S. Pat. No. 3,705,100 discloses a center-fed circular membrane having a spiral flow path. U.S. Pat. No. 4,212,743 discloses a device having divergent flow channels. German Patent No. 2,925,143 discloses a filtration apparatus having parallel blood flow paths on one side of a membrane and parallel plasma flow paths, which are perpendicular to the blood flow paths, on the opposite surface of the membrane. U.K. Patent Application No. 2,037,614 discloses a rectilinear double-membrane envelope in which the membranes are sealed together at the ends of the blood flow path. U.K. Patent Specification No. 1,555,389 discloses a circular, center-fed, double-membrane envelope in which the membranes are sealed around their peripheries. German Patent No. 2,653,875 discloses a circular, center-fed double-membrane device in which blood flows through slot-shaped filter chambers.

During plasmapheresis, it is desirable to attain high plasma separation efficiency. High plasma separation efficiency means that a large percentage of available plasma is removed. Membrane fouling, however, may impede maintenance of high separation efficiency for an extended period of time. Membrane fouling is discussed in Asanuma, Y., et al., *Proc. Euro. Soc. Artif. Organs* 6: 308, 1979 and Folstrom, R. J., et. al., *Trans. Am. Soc. Artif. Organs* 21: 602, 1975. It is believed to be a response to convective forces depositing components of the blood on the membrane. As fouling progresses, plasma flow will decline or can be maintained by increasing the difference in pressure between the blood side and plasma side of the membrane, i.e., transmembrane pressure difference. High transmembrane pressure difference may cause undesirable molecular scale sieving and blood trauma.

It is an object of this invention to provide a method for plasmapheresis by filtration which can be carried out with high plasma separation efficiency for long periods of time by passing plasma through a membrane in an efficient manner, and apparatus therefor.

BRIEF DESCRIPTION OF THE DRAWINGS

FIG. 2a is a plot of system transmembrane pressure difference versus time.

FIG. 2b is a plot of plasma flow rate versus time and is superimposable upon FIG. 2a.

DISCLOSURE OF THE INVENTION

Figure 1:
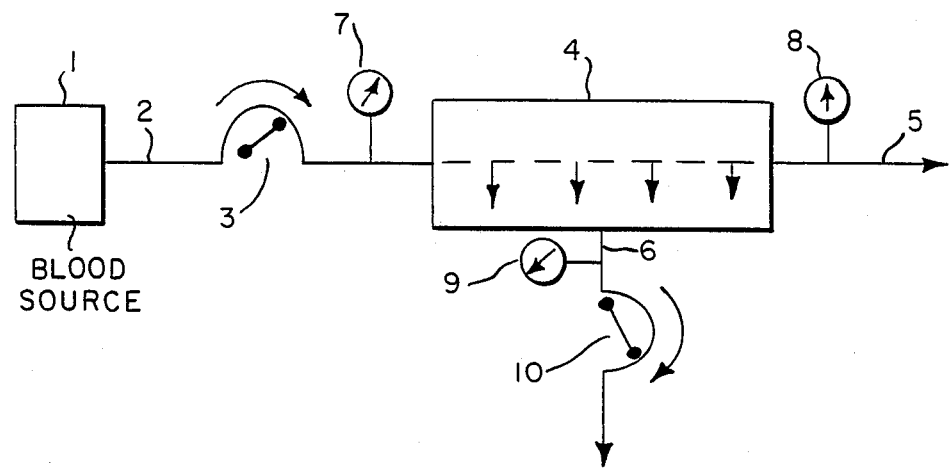
FIG. 1 is a flow diagram of the preferred embodiment of the invention.

For further comprehension of the invention and of the objects and advantages thereof, reference may be had to the following description and to the appended claims in which the various novel features of the invention are more particularly set forth.

The invention resides in the discovery that plasmapheresis by filtration through a membrane can be carried out with high plasma separation efficiency for long periods of time by conducting blood over a surface of a membrane and, in a cyclic manner, (a) passing plasma through the membrane and, when the ceiling system transmembrane pressure difference is attained, (b) reducing the flow of plasma through the membrane and reducing system transmembrane pressure difference (STMP), preferably to about zero.

The invention also resides in apparatus for carrying out plasmapheresis by filtration through a membrane which comprises a membrane, means for conducting blood over a surface of the membrane and means for passing plasma through the membrane, and means for reducing the flow of plasma through the membrane and reducing STMP, preferably to about zero, when the ceiling STMP is attained.

In its preferred embodiment, the invention resides in said process which comprises passing plasma at an accelerating rate until the threshold level is attained and in said process which further, comprises reducing the rate of acceleration preferably to about zero and, when the ceiling STMP is attained, substantially terminating the passing of plasma and reducing STMP to about zero, and in apparatus comprising means for carrying out these steps.

The invention may be best understood by reference to the following illustrative figures. Referring to FIG. 1, which illustrates the preferred scheme for carrying out the invention, blood is continuously conducted from a source 1, e.g., human donor or patient through a blood line 2, by means of a pump 3 into plasmapheresis membrane filter module 4. Within module 4, plasma is separated from the blood by filtration. Plasma-depleted blood exits from the module via line 5 while plasma exits via line 6. Pressure transducers 7, 8, 9 are located near the inlet to the module on line 2, near the plasma-depleted blood outlet on line 5 and near the plasma outlet on line 6, respectively. A plasma pump, 10, draws plasma through the membrane in the module by pumping plasma away from the membrane.

Pressure transducers 7, 8, 9 are used to monitor STMP which is defined as follows:

[(blood inlet pressure + blood outlet pressure) ÷ 2] — plasma outlet pressure.

The modifier, "system", is used to indicate that the transmembrane pressure difference being monitored is the average across the entire module and not the transmembrane pressure difference at any one point on a membrane within the module.

The preferred manner of passing plasma through the membrane and reducing the passing of plasma and reducing STMP is illustrated by FIGS. 2a and 2b. Referring to FIG. 2a, plasma is initially drawn at a slow rate. The rate of drawing is accelerated during time period 11, e.g., 5 ml-min$^{-1}$-min$^{-1}$, providing an accelerating increase in STMP. This acceleration is continued, typically for less than about 5 minutes to about 10 minutes, until the STMP reaches the threshold level 14, e.g., about 50 mm Hg (6.7 kPa), after which the rate of acceleration is reduced to zero, i.e., the plasma flow rate ($Q_f$) is maintained constant, during time period 12. Despite the constant $Q_f$, STMP continues to rise. When STMP reaches ceiling pressure 15, e.g., about 100 mm Hg (13.3 kPa), the plasma pump is turned off and STMP is thereby reduced to about zero, allowing the membrane to be cleared during time period 13, typically less than about 5 minutes. Membrane clearing during time period 13 is enhanced by the use of fouling-reducing techniques while conducting the blood over the surface of the membrane, e.g., reciprocatory pulsatile flow, high blood velocity and blood recycle.

Reciprocatory pulsatile flow is the preferred manner of conducting blood over the membrane in carrying out this invention, although it is to be noted that plasmapheresis by filtration using reciprocatory pulsatile flow is the invention of another and is disclosed and claimed in application Ser. Nos. 287,116 filed July 22, 1981; 349,371 filed Feb. 16, 1982; and 478,812 filed Mar. 30, 1983, all of which have been expressly abandoned, and 009,003 filed Jan. 28, 1987. It comprises, in summary, oscillating blood in a flow path on a surface of a membrane with a net movement of blood from inlet to outlet of the flowpath while collecting plasma which passes through the membrane. Means for carrying out this process include, e.g., a plurality of coordinated pumps and valves positioned on blood inlet, plasma-depleted blood outlet and plasma lines; pressure accumulators, or surge chambers, may also be useful. Blood recycle is a means of achieving high blood velocity which has also been shown to reduce membrane fouling.

In a preferred apparatus for carrying out the invention, the $Q_f$ is controlled electronically in response to the STMP, e.g., an electronic device such as a microprocessor which automatically accelerates $Q_f$, ceases the acceleration when the threshold level is attained, reduces $Q_f$ and STMP when the ceiling pressure is attained and repeats the cycle after a fixed duration. The threshold level is the STMP or rate of STMP increase which provides the optimal plasma separation efficiency, i.e., high $Q_f$ with a moderate rate of STMP increase without unacceptable sieving and blood trauma. If the rate of passing plasma is accelerated beyond the optimal threshold level, a very high $Q_f$ may be achieved, but STMP will rapidly increase to the ceiling pressure resulting in a short time period during which plasma is separated and, possibly, in irreversible fouling.

If the rate of passing plasma does not attain the threshold level, or does so too slowly, $Q_f$ will be undesirably low even though the ceiling STMP may be reached very slowly. The ceiling pressure is the pressure above which unacceptable fouling and blood trauma begin to occur.

Referring to FIG. 2b, $Q_f$ increases during time period 11' until the threshold level 14' is attained, after which, during time period 12', $Q_f$ is substantially constant. When STMP is reduced, $Q_f$ substantially ceases, i.e., during time period 13'. $Q_f$ resumes when the cycle is repeated.

It should be emphasized that the above description is an example only. The specified $Q_f$ acceleration rate, threshold level and ceiling pressure may not be optimal. They are typical of a plasmapheresis treatment allowing for a substantial margin of safety in avoiding blood trauma while providing acceptable plasma separation efficiency. The optimal values in a particular case may vary with several factors, e.g., module design, manner of conducting the blood over the membrane and characteristics of the blood. Further, while it is believed to be preferable to substantially terminate $Q_f$ and reduce STMP to about zero when the ceiling STMP is attained, reversing the flow of plasma or reducing STMP to below zero is not precluded, just as other variations not specifically discussed herein, e.g., irregular acceleration of $Q_f$, are not precluded.

While the preferred embodiments of the invention are described above, it is to be understood that the invention is not limited to the precise embodiments herein disclosed and that the right to all changes and modifications coming within the scope of the invention as defined in the following claims is reserved.

I claim:

1. Improved plasmapheresis comprising conducting blood over the first surface of a microporous membrane having first and second surfaces, while collecting plasma-depleted blood from the first surface and plasma which flows through the membrane (plasma flow) from the second surface, the improvement characterized in that, when the system transmembrane pressure (STMP) reaches the ceiling STMP which is the pressure above which membrane fouling and blood trauma occur, membrane fouling is cleared by substantially terminating the plasma flow while continuing the conducting of blood over the first surface, and thereafter restarting plasma flow and continuing the collection of plasma.

2. Process of claim 1 which further comprises conducting blood over the surface of the membrane using fouling-reducing techniques.

3. Process of claim 1 which further comprises conducting blood over the surface of the membrane by reciprocatory pulsatile flow.

4. Process of claim 1 which further comprises electronically controlling the plasma flow in response to the system transmembrane pressure.

5. Improved apparatus for carrying out plasmapheresis by filtration, which apparatus comprises means for conducting blood over the first surface of a microporous membrane having first and second surfaces, said means operably connected to means for collecting plasma-depleted blood from the first surface and plasma which flows through the membrane (plasma flow) from the second surface, sadi means operably connected to means for measuring system transmembrane pressure (STMP), said means operably connected to means for substantially terminating the plasma flow while blood is conducted over the first surface of the microporous membrane.

6. Apparatus of claim 5 which includes means for conducting blood over the surface of the membrane using fouling-reducing techniques.

7. Apparatus of claim 5 which includes means for conducting blood over the surface of the membrane by reciprocatory pulsatile flow.

8. Apparatus of claim 5 which includes an electronic device which controls the plasma flow in response to the system transmembrane pressure.

* * * * *